United States Patent
Kinoshita et al.

(10) Patent No.: US 6,204,393 B1
(45) Date of Patent: Mar. 20, 2001

(54) METHOD FOR CRYSTALLIZING MALEIC ACID SALT OF N-(1(S)-ETHOXYCARBONYL-3-PHENYLPROPYL)-L-ALANYL-L-PROLINE

(75) Inventors: Koichi Kinoshita; Tadashi Moroshima; Yoshifumi Yanagida; Yoshihide Fuse; Yasuyoshi Ueda, all of Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/508,801

(22) PCT Filed: Jul. 19, 1999

(86) PCT No.: PCT/JP99/03872

§ 371 Date: Mar. 17, 2000

§ 102(e) Date: Mar. 17, 2000

(87) PCT Pub. No.: WO00/05247

PCT Pub. Date: Feb. 3, 2000

(30) Foreign Application Priority Data

Jul. 21, 1998 (JP) ................................................. 10-205236

(51) Int. Cl.$^7$ .................................................. C07K 5/062
(52) U.S. Cl. .............................................................. 548/533
(58) Field of Search ............................................... 548/533

(56) References Cited

U.S. PATENT DOCUMENTS 4,374,829    2/1983    Harris et al. .......................... 424/177

FOREIGN PATENT DOCUMENTS

| 47-37921 | 9/1972 | (JP) . |
| 59-225153 | 12/1984 | (JP) . |
| 62-48696 | 3/1987 | (JP) . |
| 2-503923 | 11/1990 | (JP) . |
| WO99/05164 | 2/1999 | (WO) . |

OTHER PUBLICATIONS

Thomas J. Blacklock et al; J. Org. Chem. (1988), vol. 53, No. 4, pp. 836–844. See PCT search rpt.

*Primary Examiner*—Laura L. Stockton
(74) *Attorney, Agent, or Firm*—Armstrong, Westerman, Hattori, McLeland & Naughton, LLP

(57) ABSTRACT

A process for simply and easily crystallizing a maleate salt of N-(1(S)-ethoxycarbonyl-3-phenylpropyl)-L-alanyl-L-proline (enalapril) having a high quality out of an aqueous liquid, which comprises mixing an aqueous liquid having a pH of not less than 4 and containing N-(1(S)-ethoxycarbonyl-3-phenylpropyl)-L-alanyl-L-proline, maleic acid and a base with an amount of an acid sufficient to convert substantially all the base into a neutral salt.

12 Claims, No Drawings

METHOD FOR CRYSTALLIZING MALEIC ACID SALT OF N-(1(S)-ETHOXYCARBONYL-3-PHENYLPROPYL)-L-ALANYL-L-PROLINE

This application is a 371 of PCT/JP99/03872 filed Jul. 19, 1999.

TECHNICAL FIELD

The present invention relates to a process for economically advantageously crystallizing a maleate salt of N-(1(S)-ethoxycarbonyl-3-phenylpropyl)-L-alanyl-L-proline (hereinafter also referred to as "enalapril") of the formula (I):

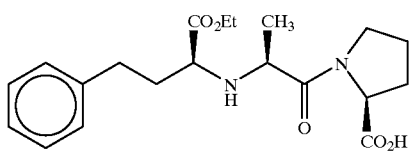

on a commercial scale in a high quality and a high yield to thereby purify the maleate salt. The N-(1(S)-ethoxycarbonyl-3-phenylpropyl)-L-alanyl-L-proline maleate salt (enalapril maleate) is a compound very useful as an antihypertensive agent.

BACKGROUND ART

A process for crystallizing a pharmacologically acceptable salt of enalapril (I), particularly enalapril maleate that the pharmacologically acceptable salt is maleate salt, is disclosed, for example, in U.S. Pat. No. 4,442,030, U.S. Pat. No. 4,374,829 and U.S. Pat. No. 5,359,086 wherein the process is conducted by recrystallization from an organic solvent such as acetonitrile. However, it is assumed that a trace amount of the organic solvent is unavoidably introduced into the final product, thus imparting undesirable characteristics to enalapril maleate which is taken in by a human being. Accordingly, the use of organic solvents should be avoided. From such a point of view, the use of an aqueous liquid would produce favorable results.

As to a process for taking enalapril maleate out of an aqueous liquid in the form of crystals, for example, Journal of Organic Chemistry, Vol. 53, 836–844(1988) discloses a process wherein enalapril maleate having a small content of N-(1(R)-ethoxycarbonyl-3-phenylpropyl)-L-alanyl-L-proline maleate which is an optical isomer that the configuration of carbon atom to which ethoxycarbonyl group bonds is different from enalapril, is obtained by recrystallizing enalapril maleate from water. However, no detail of procedure, yield, purification effect and so on is disclosed therein.

Also, U.S. Pat. No. 4,374,829 discloses a process for obtaining an enalapril salt by converting enalapril to its pharmacologically acceptable salt in water followed by an operation such as evaporation of water or freeze drying. However, the process requires a long time in its operation and accordingly have problems such as waste of time, lowering of productivity, waste of vast energy and complication of operation, so the process has many problems to be solved in production on a commercial scale.

Thus, it has been desired to provide a process for economically advantageously crystallizing enalapril maleate having a high quality directly from an aqueous liquid in a high yield.

The maleate salt of the enalapril (I) can be obtained in general by mixing enalapril and maleic acid in a suitable solvent, preferably an aqueous liquid, to produce the enalapril maleate and obtaining it in the form of crystals after forming a slurry with a high concentration by concentration, freeze drying or the like. However, in case of obtaining the crystals directly from the above aqueous liquid without applying any special procedure, it is difficult, from the point of solubility, to achieve a large amount of crystallization. In particular, in case of purification by a recrystallization method wherein enalapril maleate is once dissolved in an aqueous liquid and then recrystallized, it is particularly difficult to raise the amount of crystallization owing to solubility characteristics of enalapril maleate. For increasing the amount of crystals deposited in this recrystallization method, it is required to make the difference in the amount of dissolution large between at the time of forming the solution and at the time of crystallization. For example, in case of the cooling crystallization, a large amount of crystallization is not achieved since the change in solubility of enalapril maleate based on the difference in temperature is relatively small. Thus, it is necessary to combine it with a concentrating crystallization so as to decrease the amount of mother liquor to thereby increase the amount of crystals deposited. However, such an operation requires a long time and, therefore, it is not an advantageous process from the viewpoints of waste of time, lowering of productivity, waste of vast energy and complicated operation. Further, since the solubility of enalapril maleate is generally low even at high temperatures, the amount of the solution becomes large relatively and this brings about disadvantages such as enlargement of dissolution equipment, lowering of productivity and increase of waste water. Therefore, the application of the process to a commercial scale production requires a further improvement. Also, increase in thermal hysteresis through dissolution and concentration operations is unfavorable because it leads to a serious problem such as increase in production of impurities. However, no effective means for solving these problems has been known.

Also, in case of forming enalapril maleate in a solvent from enalapril and maleic acid and then crystallizing the maleate, there arise problems that a diketopiperazine derivative is by-produced and a carboxy derivative contaminates.

Accordingly, it is an object of the present invention to provide a simple and economically advantageous process suitable for industrial production wherein enalapril maleate having a high quality is obtained in a high yield by dissolving enalapril maleate in an aqueous liquid in a high concentration and crystallizing the maleate directly from the resulting solution.

A further object of the present invention is to provide a process for obtaining enalapril maleate having a high quality in a high yield and a high efficiency from enalapril and maleic acid.

DISCLOSURE OF INVENTION

The present inventors have found that:

(i) as a manner for obtaining a solution of enalapril maleate dissolved in an aqueous liquid in a high concentration it is effective to dissolve the maleate under a condition of a pH of not less than 4 by using a base, (ii) a large difference in solubility of enalapril maleate is obtained by mixing the aqueous liquid of pH 4 or higher obtained in (i), in which enalapril maleate is dissolved in a high concentration, with an acid to lower the pH, preferably to lower the pH to a pH 2 to 3, (iii) as a consequence, enalapril maleate having a high quality can be economically advantageously crystallized in a simple manner in a high yield merely by lowering the pH of the aqueous liquid obtained in (i) without applying any additional procedure, and at that time a salting out effect based on a neutral salt (particularly inorganic salt) produced by the acid contributes to increase in the amount of crystals deposited, and (iv) by using the process mentioned above, enalapril maleate having a low content of impurities such as N-(1(S)-carboxy-3-phenylpropyl)-L-alanyl-L-proline (hereinafter also referred to as "carboxy derivative (III)") of the formula (III):

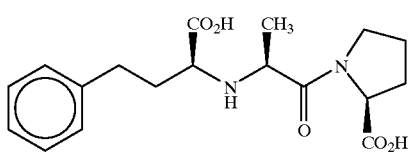

is obtained, while suppressing by-production of a diketopiperazine derivative of the formula (II):

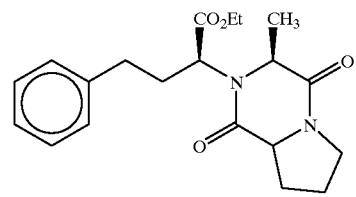

Thus, the present invention provides a process for crystallizing a maleate salt of N-(1(S)-ethoxycarbonyl-3-phenylpropyl)-L-alanyl-L-proline of the formula (I):

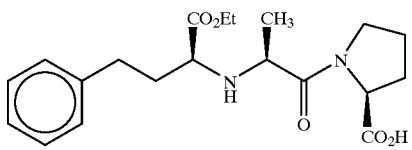

which comprises mixing an aqueous liquid having a pH of not less than 4 and containing N-(1(S)-ethoxycarbonyl-3-phenylpropyl)-L-alanyl-L-proline (I), maleic acid and a base with a sufficient amount of an acid to convert substantially all of said base into a neutral salt.

The base changes into a neutral salt by mixing of the aqueous liquid with an acid, whereby the solubility is lowered to crystallize the compound (I) as its maleate salt out of the aqueous liquid. Further, the produced neutral salt contributes to crystallization of the maleate salt by salting out effect. According to the process of the present invention, a maleate salt of N-(1(S)-ethoxycarbonyl-3-phenylpropyl)-L-alanyl-L-proline (I) having a low content of N-(1(S)-carboxy-3-phenylpropyl)-L-alanyl-L-proline of the formula (III):

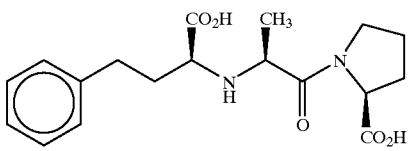

can be obtained, while restraining by-production of a diketopiperazine derivative of the formula (II):

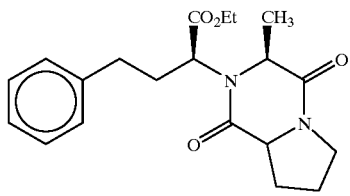

BEST MODE FOR CARRYING OUT THE INVENTION

An aqueous liquid having a pH of at least 4 and containing enalapril, maleic acid and a base can be obtained, for example, by dissolving enalapril maleate in an aqueous liquid under a condition of a pH of not less than 4. Alternatively, it can also be obtained by dissolving enalapril and maleic acid respectively in an aqueous liquid. In case of dissolving enalapril maleate in water, the pH of the resulting solution becomes 2 to 3 and, therefore, the pH of the aqueous liquid is usually adjusted to a pH of not less than 4 by using a base.

The enalapril (I) and its maleate salt to be used can be prepared, for example, by a process disclosed in Japanese Patent Publication Kokai No. 62-48696, U.S. Pat. No. 4,374,829 and WO99/05164.

The base used for dissolving the enalapril maleate in an aqueous liquid under a condition of a pH of not less than 4 is not particularly limited, and can be selected from inorganic bases and organic bases. Examples of the base are, for instance, inorganic bases such as hydroxides, carbonates and bicarbonates of alkali metals or alkaline earth metals, and organic bases such as quaternary ammonium hydroxides. Representative examples of these bases are, for instance, an alkali metal hydroxide such as sodium hydroxide, potassium hydroxide or lithium hydroxide, an alkali metal carbonate such as sodium carbonate, potassium carbonate or lithium carbonate, an alkali metal hydrogencarbonate such as sodium bicarbonate or potassium bicarbonate, an alkaline earth metal hydroxide such as magnesium hydroxide or calcium hydroxide, a quaternary ammonium hydroxide such as tetramethylammonium hydroxide, tetraethylammonium hydroxide, tetrapropylammonium hydroxide, tetrabutylammonium hydroxide, tetraamylammonium hydroxide, tetrahexylammonium hydroxide or benzyltrimethylammonium hydroxide, and the like. Other bases than the above can also be used.

It is advantageous to use bases which are inexpensive and easy to handle and treat waste water and, in addition, which can exhibit a higher salting out effect based on a neutral salt formed when mixed with an acid. For example, preferable are inorganic bases, particularly an alkali metal hydroxide such as sodium hydroxide, potassium hydroxide or lithium hydroxide, an alkali metal carbonate such as sodium carbonate, potassium carbonate or lithium carbonate, and an alkali metal hydrogencarbonate such as sodium bicarbonate or potassium bicarbonate. Of these, alkali metal hydroxides, especially sodium hydroxide and potassium hydroxide, are more preferable. From the viewpoint of operability or the like, preferably the inorganic bases are used in the form of an aqueous solution. For example, it is advantageous to use an aqueous solution of an alkali metal hydroxide having a concentration of 2 to 20 N, preferably 5 to 20 N. The bases may be used alone or in admixture thereof.

The base is used in an amount sufficient to adjust the pH of an aqueous liquid containing enalapril and maleic acid to 4 or more, for example, in an amount necessary to dissolve enalapril maleate in an aqueous liquid under a condition of a pH of not less than 4. In general, the amount of the base used is equal to or greater than molar equivalents (acid-base equivalent) of the maleic acid used. In case of an embodiment wherein enalapril maleate is dissolved, the amount is equal to or greater than molar equivalents of the maleate. However, the use of the base in an amount necessary to maximize the salting out effect based on a neutral salt formed when mixing with an acid in the subsequent step can also be suitably utilized from the viewpoint of increasing the amount of crystals deposited.

From such a point of view, more preferably the pH of the aqueous liquid at the time of dissolution is not less than 5, though the process can be well practiced if the pH is not less than 4. When the pH of the aqueous liquid is within the above range, it is possible to dissolve enalapril maleate in a high concentration. It is unfavorable to raise the pH to more than necessary at the time of dissolution, since it brings about by-production of the carboxy derivative (III) by hydrolysis of ethoxycarbonyl group. Therefore, in general, it is preferable that the pH of the aqueous liquid at the time of dissolution is at most 10, especially at most 8, more especially at most 7.

The aqueous liquid is substantially water, but may be a mixture of water and an organic solvent contained within a range exerting no bad influence.

The concentration of enalapril in the aqueous liquid cannot be generically specified since it varies depending on operation temperature, kind and amount of the base used, composition of the aqueous liquid, and kind and concentration of a coexisting inorganic salt, but it can be freely selected within the range capable of forming a uniform solution. In order to increase the amount of crystals deposited in the subsequent crystallization step, it is preferable to prepare a solution having a concentration as high as possible. For example, the solution can be used at a saturation concentration under operation conditions such as pH and temperature or in the vicinity of the saturation concentration or in the supersaturated state. Practically, the process can be carried out at a high concentration of at least 10%, preferably at least 20%, more preferably at least 30%.

The concentration of maleic acid is within a range causing no trouble in the practical operation, wherein maleic acid can be used in such an amount as capable of converting at least all of enalapril into its maleate salt, that is, in an amount equimolar with or larger than enalapril. In case of an embodiment wherein enalapril maleate is dissolved in an aqueous liquid, maleic acid is present in an amount equimolar with enalapril.

The operation temperature for preparing an aqueous liquid having a pH of at least 4 and containing enalapril, maleic acid and a base is not particularly limited, since according to the process of the present invention a high temperature is not particularly required in obtaining a solution with a high concentration and the dissolution can be achieved in high concentrations even at a relatively low temperature. Practically, the operation can be made usually at a temperature of not higher than 70° C., preferably not higher than 60° C., more preferably not higher than 50° C., and at a temperature that the solvent does not freeze. In particular, the operation can be suitably made at a temperature of about 20 to about 40° C. The same operation temperature as above is also applicable to the embodiment wherein the solution is prepared by dissolving enalapril maleate.

Enalapril maleate can be crystallized in a high yield by mixing the aqueous liquid having a pH of at least 4 and containing enalapril, maleic acid and a base in high concentrations with an acid to lower the pH.

The acid is used in an amount capable of converting substantially all of the base in the aqueous liquid into a neutral salt. By such an amount of an acid, all enalapril is turned to the maleate salt and the pH of the aqueous liquid becomes a pH in the vicinity of the pH that enalapril maleate itself has. This pH is generally from 2 to 3 and maximizes the amount of crystals deposited. The use of an acid in an amount larger than the above is not always preferable, since the crystallized maleate salt is converted into a salt with the acid used to be dissolved again, thus resulting in decrease of the amount of crystals. Also, the use of an acid in an amount smaller than the above is not always preferable, since in many cases enalapril is not crystallized as the maleate salt to remain in the aqueous liquid, thus lowering the amount of crystals deposited.

The acid to be used is not particularly limited, but a strong acid is preferred from the viewpoint of practical use. In particular, it is advantageous to use a combination of a base with an acid which can enhance the salting out effect of the neutral salt formed with the base used. From such a point of view, a mineral acid such as hydrochloric acid, sulfuric acid or phosphoric acid is preferable. Also, from the viewpoints of economy and easiness in treating waste water, hydrochloric acid and sulfuric acid are more preferable, and hydrochloric acid is the most preferable. Maleic acid can also be suitably used for this purpose. The acids may be used alone or in admixture thereof. Also, the acids may be used as they are or may be diluted with an aqueous liquid to use in the form of a solution.

Preferable combinations of base and acid are a combination of sodium hydroxide and hydrochloric acid and a combination of potassium hydroxide and hydrochloric acid.

The operation temperature for crystallizing enalapril maleate by mixing the above-mentioned aqueous liquid with an acid is not generically specified, since it varies depending on the composition of the aqueous liquid, the operation manner and the like. Practically, the crystallization is carried out at a temperature which is below the boiling point of the aqueous liquid and that the aqueous liquid does not freeze. Although the temperature is not required to unnecessarily elevate to a high temperature, the crystallization at a higher temperature provides the crystals with desirable characteristics such as excellent filterability and drying property of the crystals and excellent removability of impurities. From such a point of view, the operation temperature is preferably from 40 to 70° C., more preferably in the vicinity of 60° C. After conducting the crystallization operation at such a temperature, the aqueous liquid is finally cooled to a temperature of not more than 20° C., preferably not more than 10° C., whereby the amount of crystals can be increased.

In general the mixing of the aqueous liquid and an acid can be practiced by adding the acid to the aqueous liquid having a pH of at least 4 and containing enalapril, maleic acid and a base, but a manner of adding the aqueous liquid to an acid is also adaptable. In particular, the latter manner can be suitably used also from the viewpoint that when the addition operation is practiced at a higher temperature, impartment of heat to the solution until the maleate salt is crystallized out can be decreased.

In the mixing operation, the time for adding all of the acid or the aqueous liquid is generally at least ¼ hour, preferably at least ⅓ hour, more preferably at least ½ hour. There is no limitation in the upper limit of the addition time, but the addition time is generally at most 20 hours, preferably at most 10 hours, more preferably at most 5 hours, from the viewpoints of productivity and the like.

In the operation for crystallizing enalapril maleate out of the aqueous liquid, it is also an important factor for increasing the amount of crystals deposited that the salting out effect of a neutral salt formed from the base and the acid present in the aqueous liquid, particularly the salting out effect of an inorganic salt, can be effectively utilized. The concentration of the inorganic salt in the aqueous liquid cannot be generically specified since it varies depending on the concentration, temperature and manner in crystallization operation and the kind of the inorganic salt. However, it is important in promoting a good crystal growth not to excessively raise the concentration of inorganic salt during the growth. In general, the concentration of the inorganic salt is at most 15% by weight, especially at most 10% by weight, and usually a concentration of 3 to 8% by weight is preferable. The process of the present invention is also advantageous in that by the operation of mixing the aqueous liquid and the acid, the concentration of inorganic salt is favorably increased as the crystallization of the maleate salt proceeds. Although the concentration of inorganic salt is inevitably increased and finally a sufficient salting out effect is obtained, an additional inorganic salt may be added as occasion demands. The salting out effect of an inorganic salt such as sodium chloride or potassium chloride is particularly excellent.

The crystals of the maleate salt deposited can be easily taken out in a high yield by a simple operation such as filtration without any special operation. The use of an aqueous liquid as a solvent in the above operations is advantageous also in that upon obtaining the maleate salt of enalapril (I), contamination of the product with the inorganic salt coexisting in the system can be effectively minimized without applying any special treatment.

The practice of the above process in an aqueous liquid is also advantageous in that by-production of a diketopiperazine derivative of the formula (II):

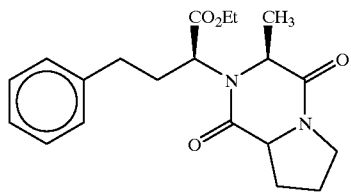

(II)

can be effectively restrained in a series of operations. Further, the purification according to the above process is also effective for removal of N-(1(S)-carboxy-3-phenylpropyl)-L-alanyl-L-proline of the formula (III):

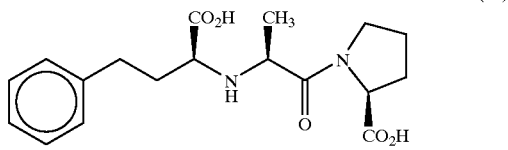

(III)

which is well known as an impurity produced by hydrolysis of the ethoxycarbonyl group of enalapril, and the content thereof in the obtained enalapril maleate can be decreased to a negligible level. Like this, enalapril maleate having a low content of these impurities can be effectively obtained in a high yield and a high quality in a simple manner.

The present invention is more specifically explained by means of the following examples, but it is to be understood that the present invention is not limited to these examples.

In the examples, the purity and the contents of carboxy derivative (III) and diketopiperazine derivative (II) were measured by HPLC and determined by an absolute calibration method. The measurement conditions of HPLC are as follows:

Column: FINEPAK SIL C18-5 (trade mark, 4.6 mm×25 cm, product of Nippon Bunkoh Kabushiki Kaisha)
Solvent: 0.1M $KH_2PO_4$ (pH 2.8)/$CH_3CN$ (70:30 by volume)
Flow rate: 1.0 ml/minute
Temperature: 45° C.
Detection condition: UV 210 nm

EXAMPLE 1

To 200 ml of $H_2O$ kept at 20° C. was added 56.2 g (0.114 mole) of N-(1(S)-ethoxycarbonyl-3-phenylpropyl)-L-alanyl-L-proline maleate salt containing 0.2% by weight of carboxy derivative (III). The maleate salt was dissolved in water by adding 32.1 g (0.241 mole) of a 30% by weight aqueous solution of NaOH to this mixture with stirring to adjust to pH 6.0±0.5. To the resulting solution was added dropwise 25.1 g (0.241 mole) of conc. hydrochloric acid over 2 hours to adjust to pH 2.3'0.5, and the solution was then cooled to 0° C. over 4 hours. The resulting precipitate was filtered and washed twice with 70 ml of cold water kept at a temperature of 0 to 3° C. The obtained wet crystals were dried under vacuum (20 to 50° C., 30 mmHg→1 mmHg) to give 51.0 g (yield 91%) of N-(1(S)-ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

EXAMPLE 2

To 120 ml of $H_2O$ kept at 30° C. was added 33.0 g (0.067 mole) of N-(1(S)-ethoxycarbonyl-3-phenylpropyl)-L-alanyl-L-proline maleate salt containing 0.2% by weight of carboxy derivative (III). The maleate salt was dissolved in water by adding 18.1 g (0.136 mole) of a 30% by weight aqueous solution of NaOH to this mixture with stirring to adjust to pH 6.0±0.5. The resulting solution was heated to 60° C., and thereto was added dropwise 14.3 g (0.137 mole) of concentrated hydrochloric acid over 2 hours to adjust to pH 2.3±0.5. The mixture was then cooled to 0° C. over 4 hours, and thereto was added 12.0 g of NaCl and the stirring was further continued for 2 hours. The resulting precipitate was filtered and washed twice with 40 ml of cold water kept at a temperature of 0 to 3° C. The obtained wet crystals were dried under vacuum (20 to 50° C., 30 mmHg→1 mmHg) to give 30.4 g (yield 92%) of N-(1(S)-ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

EXAMPLE 3

To 180 ml of H$_2$O kept at 30° C. was added 59.7 g (0.121 mole) of N-(1(S)-ethoxycarbonyl-3-phenylpropyl)-L-alanyl-L-proline maleate salt containing 0.2% by weight of carboxy derivative (III). The maleate salt was dissolved in water by adding 32.4 g (0.243 mole) of a 30% by weight aqueous solution of NaOH to this mixture with stirring to adjust to pH 6.0±0.5. The resulting solution was added dropwise to 44.4 g (0.244 mole) of a 20% by weight aqueous solution of HCl kept at 60° C. over 4 hours to adjust to pH 2.3±0.5, and was then cooled to 0° C. over 3 hours. The resulting precipitate was filtered and washed twice with 70 ml of cold water kept at a temperature of 0 to 3° C. The obtained wet crystals were dried under vacuum (20 to 50° C., 30 mmHg 1 mmHg) to give 55.2 g (yield 92%) of N-(1(S)-ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

EXAMPLE 4

To 155 ml of H$_2$O kept at 40° C. was added 59.7 g (0.121 mole) of N-(1(S)-ethoxycarbonyl-3-phenylpropyl)-L-alanyl-L-proline maleate salt containing 0.2% by weight of carboxy derivative (III). The maleate salt was dissolved in water by adding 16.2 g (0.122 mole) of a 30% by weight aqueous solution of NaOH to this mixture with stirring to adjust to pH 5.2±0.5. The resulting solution was added dropwise to 46.7 g (0.121 mole) of a 30% by weight aqueous solution of maleic acid kept at 60° C. over 1 hour to adjust to pH 2.5±0.5, and was then cooled to 0° C. over 4 hours. The resulting precipitate was filtered and washed twice with 70 ml of cold water kept at a temperature of 0 to 3° C. The obtained wet crystals were dried under vacuum (20 to 50° C., 30 mmHg→1 mmHg) to give 56.2 g (yield 94%) of N-(1(S)-ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

EXAMPLE 5

To 200 g (0.1 17 mole) of a 22% by weight aqueous solution of N-(1(S)-ethoxycarbonyl-3-phenylpropyl)-L-alanyl-L-proline maleate salt containing 0.2% by weight of carboxy derivative (III) kept at 20° C. was added 13.8 g (0.119 mole) of maleic acid over 1 hour, while gradually adding a 30% by weight aqueous solution of NaOH to keep the pH at 6.2±0.5. The amount of the 30% by weight aqueous solution of NaOH required in this operation was 34.3 g (0.257 mole). The obtained solution was added dropwise to 47.1 g (0.258 mole) of a 20% by weight aqueous solution of HCl kept at 60° C. over 6 hours to adjust to pH 2.3±0.5, and was then cooled to 0° C. over 3 hours. The resulting precipitate was filtered and washed twice with 70 ml of cold water kept at a temperature of 0 to 3° C. The obtained wet crystals were dried under vacuum (20 to 50° C., 30 mmHg→1 mmHg) to give 52.4 g (yield 91%) of N-(1(S) -ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

COMPARATIVE EXAMPLE

To 400 ml of water was added 24.4 g (0.050 mole) of N-(1(S)-ethoxycarbonyl-3-phenylpropyl)-L-alanyl-L-proline maleate salt containing 0.2% by weight of carboxy derivative (III), and it was dissolved in water by heating at 60° C. (pH 2.5±0.5). The obtained solution was cooled to 0° C. over 4 hours with stirring, and was further stirred for 2 hours. The resulting precipitate was filtered and washed twice with 30 ml of cold water kept at a temperature of 0 to 3° C. The obtained wet crystals were dried under vacuum (20 to 50° C., 30 mmHg→1 mmHg) to give 17.8 g (yield 73%) of N-(1(S)-ethoxycarbonyl-3-phenylpropyl)-L-alanyl-L-proline maleate salt. The purity was not less than 99%, and the content of each of carboxy derivative (III) and diketopiperazine (II) was not more than 0.05% by weight.

Industrial Applicability

According to the process of the present invention, enalapril maleate having a high quality can be crystallized out of an aqueous liquid in a high yield in a simple manner. That is to say, according to the process of the present invention, enalapril maleate can be purified to effectively remove impurities such as carboxy derivative (III), while advantageously suppressing by-production of diketopiperazine derivative (II).

What is claimed is:

1. A process for crystallizing a maleate salt of N-(1(S)-ethoxycarbonyl-3-phenylpropyl)-L-alanyl-L-proline of the formula (I):

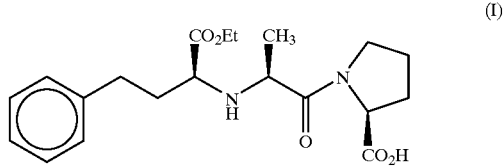

(I)

which comprises mixing an aqueous liquid having a pH of not less than 4 and containing N-(1(S)-ethoxycarbonyl-3-phenylpropyl)-L-alanyl-L-proline (I), maleic acid and a base with a sufficient amount of an acid to convert substantially all of said base into a neutral salt.

2. The process of claim 1, wherein based on N-(1(S)-ethoxycarbonyl-3-phenylpropyl)-L-alanyl-L-proline (I), at least equimolar amount of said maleic acid and at least equivalent amount of said base are present in said aqueous liquid having a pH of not less than 4.

3. The process of claim 1, wherein said aqueous liquid having a pH of not less than 4 is prepared by dissolving a maleate salt of N-(1(S)-ethoxycarbonyl-3-phenylpropyl)-L-alanyl-L-proline (I) in an aqueous liquid kept at a pH of not less than 4 with said base.

4. The process of claim 1, wherein said mixing is carried out by adding said acid to said aqueous liquid to convert said base into a neutral salt.

5. The process of claim 1, wherein said mixing is carried out by adding said aqueous liquid to said acid to convert said base into a neutral salt.

6. The process of any of claims 1 to 5, wherein said base is an alkali metal hydroxide.

7. The process of any of claims 1 to 5, wherein said acid is a mineral acid.

8. The process of claim 7, wherein said mineral acid is hydrochloric acid.

9. The process of any of claims 1 to 5, wherein said acid is maleic acid.

10. The process of any of claims 1 to 5, wherein said maleate salt is crystallized out while mixing said aqueous liquid and said acid at a temperature of 40 to 70° C.

11. The process of any of claims 1 to 5, wherein the pH of said aqueous liquid after the completion of mixing with said acid is from 2 to 3.

12. The process of any of claims 1 to 5, characterized by crystallizing a maleate salt of N-(1(S)-ethoxycarbonyl-3-phenylpropyl)-L-alanyl-L-proline (I) having a low content of N-(1(S)-carboxy-3-phenylpropyl)-L-alanyl-L-proline of the formula (III):

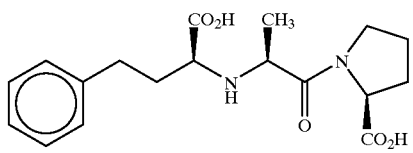

(III)

out of an aqueous liquid having a pH of not less than 4 and containing N-(1(S)-ethoxycarbonyl-3-phenylpropyl)-L-alanyl-L-proline (I), maleic acid and a base, while suppressing by-production of a diketopiperazine derivative of the formula (II):

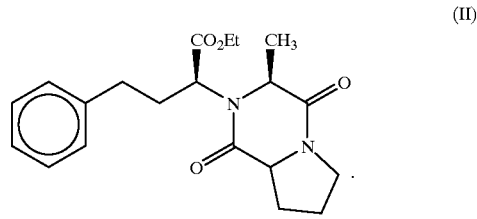

(II)

* * * * *